United States Patent [19]
Stossel

[11] Patent Number: 4,944,764
[45] Date of Patent: Jul. 31, 1990

[54] HIP PROSTHESIS

[75] Inventor: Clifford A. Stossel, Kent, England

[73] Assignee: Headcorn Instrumentation Ltd., Kent, England

[21] Appl. No.: 205,835

[22] Filed: Jun. 13, 1988

[51] Int. Cl.⁵ ............................ A61F 2/32; A61F 1/04
[52] U.S. Cl. ......................................... 623/23; 606/62
[58] Field of Search ....................... 623/16, 18, 20, 21, 623/22, 23; 128/92 Y, 92 YZ

[56] References Cited

U.S. PATENT DOCUMENTS

| | | | |
|---|---|---|---|
| 3,067,740 | 12/1962 | Haboush | 623/23 |
| 3,818,512 | 6/1974 | Shersher | 623/23 |
| 3,906,550 | 9/1975 | Rostoker et al. | 623/23 |
| 4,310,931 | 1/1982 | Muller | 623/23 |
| 4,488,319 | 12/1984 | von Recum | 623/23 |
| 4,546,501 | 10/1985 | Gustilo et al. | 623/23 |

FOREIGN PATENT DOCUMENTS

| | | | |
|---|---|---|---|
| 2854334 | 6/1960 | Fed. Rep. of Germany . | |
| 2558446 | 12/1975 | Fed. Rep. of Germany | 623/23 |
| 2839093 | 3/1980 | Fed. Rep. of Germany | 623/23 |
| 2599245 | 12/1987 | France . | |
| 1371335 | 10/1974 | United Kingdom . | |
| 2118043 | 10/1983 | United Kingdom . | |
| 2197204 | 5/1988 | United Kingdom . | |

OTHER PUBLICATIONS

"The Journal of Bone and Joint Surgery", British vol. 67-B (1985); Number Three (May).
"Huckstep Intramedullary Compression Nail", Downs Surgical PLC (1985).
"Huckstep Nail System", Downs Surgical Limited (1987).

Primary Examiner—David J. Isabella
Attorney, Agent, or Firm—Oliff & Berridge

[57] ABSTRACT

A hip prosthesis comprises a generally cylindrical elongate shaft adapted for insertion into the femur of a subject, and a generally spherical head mounted on the shaft via a generally cylindrical neck, the dimensions of the head, neck and shaft being defined. The proximal end of the shaft is spaced by 0.5-1.5 cm from the plane normal to the longitudinal axis of the shaft and through the center of the head, to avoid abduction. The center of the head is offset by no more than 4.25 cm from the longitudinal axis of the shaft, to minimise damage to the subject during insertion of the prosthesis.

1 Claim, 1 Drawing Sheet

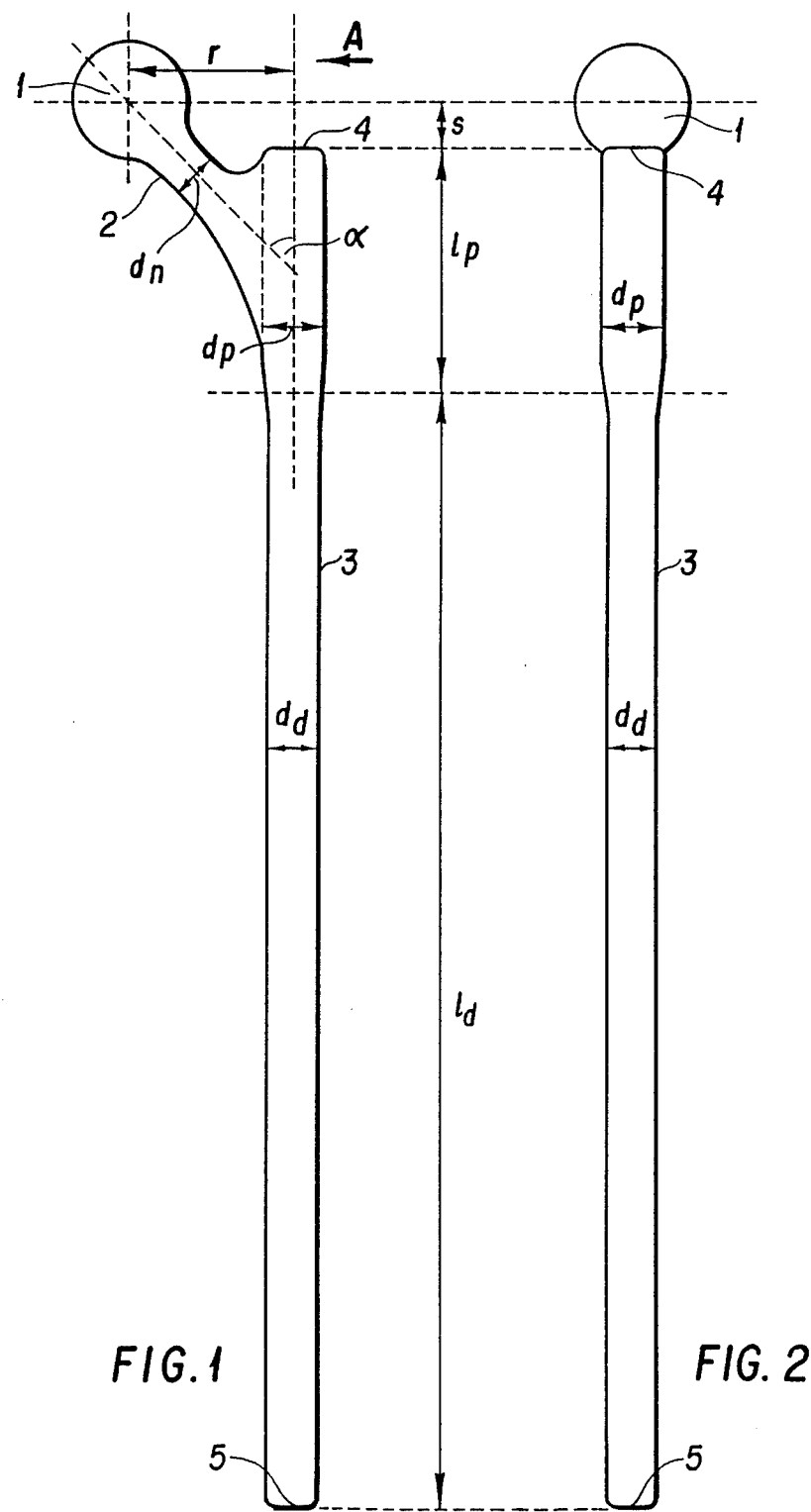

HIP PROSTHESIS

FIELD OF THE INVENTION

This invention relates to hip prostheses.

BACKGROUND OF THE INVENTION

Hip prostheses are widely used and in great demand. Conventionally, such prostheses have been designed as a more or less simple replacement for the upper end of a femur, and comprise a head mounted on a shaft which is cemented to the remaining, lower part of the femur. Even if considerable trouble and expense is taken to ensure that the prosthesis has a shape which exactly replaces the upper part of the femur, it is difficult or impossible to ensure that the prosthesis and the remaining part of the femur are joined to provide an exact replacement of the bone as a whole.

The fixing of prostheses to existing bone has recently been facilitated by the introduction of the so-called huckstep nail. A huckstep nail comprises an elongate shaft which is inserted into the remaining bone. This allows for greater precision in fixing the relative positions of the distal end of the nail and the remaining bone, and can be used even when the remaining bone has suffered considerable necrosis following, cancer. Kits for inserting and fixing huckstep nails are available.

PRIOR ART

I have already devised a hip prosthesis, based on the huckstep nail principle, which has been made and used in at least one patient. The known prosthesis is perhaps best described, although they illustrate an embodiment of the present invention, with respect to the accompanying drawings. The drawings are described below in more detail, but by comparison with the drawings and that description, two essential differences possessed by the known prosthesis were that the length s was zero and that the distance r was about 4.5 cm. The consequence of s=0 was that, after fitting, abduction of the leg was prevented. The consequence of r being as great as 4.5 cm was that the incision which had to be made to insert the prosthesis was long, and thereby liable to be difficult to stitch.

OBJECT OF THE INVENTION

It is an object of the present invention to overcome the problems associated with the known prosthesis.

SUMMARY OF THE INVENTION

A novel hip prosthesis comprises a generally spherical head, a generally cylindrical neck and a generally cylindrical elongate shaft.

The shaft is about 18 cm to about 40 cm long. Its distal end is for insertion into the femur of a subject in need of the prosthesis. A distal portion of the shaft has an outer diameter of about 1.3 cm to about 1.5 cm. A relatively enlarged and shorter proximal portion of the shaft, less than 9.5 cm long, has an outer diameter of about 1.4 cm to about 1.6 cm.

The neck of the prosthesis is integrally mounted on the enlarged, proximal portion of the shaft. The angle between the respective longitudinal axes of the neck and the shaft is about 45°. The head of the prosthesis is integrally mounted on the neck. The head has a diameter of about 2.25 cm to about 5.5 cm.

The novel prosthesis has two particularly important features: (i) the proximal end of the shaft is spaced by between about 0.5 cm and about 1.5 cm from the plane defined by the center of the head and normal to the longitudinal axis of the shaft; and (ii) the center of the head is offset by between about 3.5 cm and about 4.25 cm from the longitudinal axis of the shaft.

DESCRIPTION OF THE DRAWINGS

For the purpose of illustration only, FIGS. 1 and 2 of the accompanying drawings show different side views of an embodiment of the invention (to scale). FIG. 2 is a view from the direction indicated by the arrow A in FIG. 1.

DESCRIPTION OF THE INVENTION

FIGS. 1 and 2 show a hip prosthesis comprising a generally spherical head 1, a generally cylindrical neck 2 and a generally cylindrical elongate shaft 3. The shaft 3 has a proximal end 4 and a distal end 5. The shaft 3 includes a relatively short, wide proximal portion having an outer diameter $d_p$ (e.g. 1.4 cm) and a length $l_p$ (e.g. 6.5 cm). The shaft 3 also has a relatively long and narrow distal portion having an outer diameter $d_d$ (e.g. 1.25 cm) and a length $l_d$ (e.g. 26.5 cm).

The proximal and distal portions of the shaft 3 merge over a length of about 1 cm. The total length of the shaft of the illustrated embodiment is 33 cm.

The neck 2 has an outer diameter $d_n$ (e.g. 1.25 cm) but which widens at its base and merges into the shaft 3, such that the two components are essentially integral, and cannot easily be broken apart. The respective longitudinal axes of the neck 2 and the shaft 3 are at an angle $\alpha$ (e.g. 45°).

The head 1 is securely mounted on the neck 2. The center of the head 1 is displaced by a distance r (e.g. 4 cm) from the longitudinal axis of the shaft 3. Further, a plane through the center of the head 1 and normal to the longitudinal axis of the shaft 3 is at a distance s (e.g. 1 cm, and usually less than the radius of the head from the distal end 4 of the shaft 3.

An embodiment of the invention having the particular dimensions given may not always be suitable for use as a hip prosthesis, depending on the particular patient and the degree of necrosis. When a patient sustains a fracture of the upper end of the femur of such severity that replacement of the femoral head and neck are necessary, the head diameter is as illustrated, e.g. 2.5 cm. Where the articular cartilage of the acetabulum is in good condition, it is not necessary to excise it and insert an artificial acetabular cup. For such patients, a prosthesis having a head diameter in the upper range, between about 3.5 and 5.5 cm, is used.

The illustrated prosthesis is nevertheless satisfactory in a large number of cases. Accordingly, any given hospital can budget for a continuing supply of such prostheses, in the knowledge that they will all be used. A further advantage is that the ready availability of a widely compatible hip prosthesis reduces the length, and therefore the cost, of pre-operation patient care.

A prosthesis of the invention can be made of any suitable rigid, conventional material. The shaft and neck are preferably metal tubes formed by machining or, preferably, forging. The head may be of any suitable synthetic material known for use in replacement joints.

A concentric reaming technique may be used for blind intra-medullary nailing, after femoral fracture at one end of the lengthened segment. Following femoral lengthening, there is a danger of fracture at one end of the lengthened segment. The lengthened segment is usually not perfectly in alignment with the original femoral shaft. Any angulation makes union, less likely and loses length. The insertion of a kuntscher intramedullary nail regains alignment and length. Further, the medulla is often closed over at each end of the lengthened segment. To allow the reamer to pass down the femur, an extensive open operation may then be required. Concentric reaming avoids the need to open and displace the bone and may allow the nailing, to be done blind. The principle is that the reamer centers the drill to prevent it penetrating the side of the bone. The drill then acts as a guide wire to center the reamer, so that they leapfrog down the bone, both being powered.

Insertion of the novel prosthesis may follow the removal of a previous prosthesis, in which case it is likely that there will be some residual cement in the distal femoral shaft. For most prostheses, that residue is usually to a depth of some 17 cm from the proximal tip of the greater trochanter. It is also usual for the femoral shaft internal diameter beyond the tip of the previously inserted prosthesis to be somewhat smaller than at a more proximal area where some currettage or rasping has previously taken place.

In the operative technique, in this case, it is therefore essential to, center a drill in the femoral shaft to penetrate the distal cement. This is done using protek centering sleeves and long Protek drills. These are initially used on a hand drill but a slow air-powered drill should be available. If there is difficulty centering this drill, or if it will not penetrate, it may then be necessary to use a concentric reaming technique. This involves using a drill-pointed ,guide wire attached to one drill going down the center of a flexible reamer. The drill pointed guide wire is then used to penetrate into the cement to a depth of up to 1 cm. The flexible reamer is then used to remove the cement around the guide wire tip. It is usually to change the reamer to a smaller one than that used for centering the guide wire, so that the chances of breaking the femur are reduced. In this way, gradual progression distally down the femur can be achieved in, say, 1 cm steps. A long curette is then used to remove any debris from the distal femoral shaft. The flexible reamers are used then to expand the interior of the distal femoral shaft to as close to 1.6 cm as possible.

It is then possible to test the prosthesis down the femoral shaft. It may well be found that the whole length of the prosthesis cannot be inserted unless the femur has fractured. To this end, an ordinary huckstep nail can be used to test the length of the femoral shaft which is available to receive the prosthesis.

If the prosthetic length which can be fitted into the femoral shaft is less than the overall length of the prosthesis available, then obviously the prosthesis will have to be cut. A sharp hacksaw can be used and, in order to stabilise the prosthesis for the cut to be made, an A/0 bending press may be useful.

Once the prosthesis has been cut and it is seen that it can be inserted far enough down the femoral shaft, it is then rotated so that slight anteversion is obtained. One screw is then inserted through the femoral shaft and the prosthesis distally. This then fixes the rotation of the prosthesis in relation to the femoral shaft. Once this has been done, the prosthesis cannot be rotated in relation to the femoral shaft without new drill holes being made. As this would probably be impossible without a considerable alteration in length of the prosthesis, so that the drill holes did not overlap, it is important to use just one screw in place as a means of assessing the correct rotation of the prosthesis in the femoral shaft.

If the femoral shaft has not been fractured, it is advisable that five screws be used to fix the prosthesis in the femoral shaft. It is noted that no transverse drill hole to receive a screw is made in the prosthesis closer than 9 cm to the proximal end. This avoids a stress raiser at areas of the prosthesis where an angular strain is being received and where the tapering of the bulbous proximal end is reduced to the distal shaft dimension of 1.25 cm.

If the femoral shaft is fractured, then the initial screw is inserted through the femoral shaft and prosthesis distal to the fracture. Rotational alignment marks are made either side of the fracture site, to check that the test reduction of the prosthesis will ensure that the greater trochanter is satisfactorily placed. Once this has been done, a compression device can be used to compress the fracture site. The rest of the insertion of the prosthesis is done in the usual manner for a huckstep nail.

What is claimed is:

1. A hip prosthesis consisting essentially of a generally spherical head, a generally cylindrical neck and a generally cylindrical elongate straight shaft; said shaft being about 18 cm to about 40 cm long, said shaft having a proximal end and a distal end for insertion into the femur of a subject in need of the prosthesis, wherein a distal portion of said shaft has an outer diameter of about 1.3 cm to about 1.5 cm and a proximal portion of said shaft, less than 9.5 cm long and shorter than said distal portion, has an outer diameter of about 1.4 cm to about 1.6 cm and which is greater than said distal portion; wherein said neck is integrally mounted on said proximal portion of said shaft, the angle between the respective longitudinal axes of said neck and said shaft being about 45°; wherein said head, integrally mounted on said neck, has a diameter of about 2.25 cm to about 5.5 cm; wherein said proximal end of said shaft is spaced by between about 0.5 cm and about 1.5 cm from the plane defined by the center of said head and normal to the longitudinal axis of said shaft; and wherein said center of said head is offset by between about 3.5 cm and about 4.25 cm from said longitudinal axis of said shaft.

* * * * *